United States Patent [19]

Angerbauer et al.

[11] Patent Number: 5,502,199

[45] Date of Patent: Mar. 26, 1996

[54] PROCESS FOR PREPARING SODIUM 3R,5S-(+)-ERYTHRO-(E)-7-[4-(4-FLUOROPHENYL)-2,6-DIISOPROPYL-5-METHOXYMETHYL-PYRID-3-YL]-3,5-DIHYDROXY-HEPT-6-ENOATE

[75] Inventors: Rolf Angerbauer, Wuppertal; Rolf Grosser, Leverkusen, both of Germany; Werner Hinsken, Clayton, N.C.; Joachim Rehse, Wuppertal, Germany

[73] Assignee: Bayer Aktiengesellschaft, Leverkusen, Germany

[21] Appl. No.: 214,894

[22] Filed: Mar. 17, 1994

[30] Foreign Application Priority Data

Mar. 24, 1993 [DE] Germany .......................... 43 09 553.4

[51] Int. Cl.⁶ ................................................. C07D 213/30
[52] U.S. Cl. ............................................................ 546/342
[58] Field of Search ............................................. 546/342

[56] References Cited

U.S. PATENT DOCUMENTS 5,006,530  4/1991  Angerbauer et al. .................... 514/277
5,117,038  5/1992  Haug et al. .................................. 560/55
5,169,857  12/1992  Angerbauer et al. ................... 514/344
5,177,080  1/1993  Angerbauer et al. ................... 514/277

OTHER PUBLICATIONS

Hoffman et al. Journal of Medicinal Chemistry vol. 29, #2. pp. 159–169. 1986.

*Primary Examiner*—Jane Fan
*Attorney, Agent, or Firm*—Sprung Horn Kramer & Woods

[57] ABSTRACT

Enantiomerically pure sodium 3R,5S-(+)-erythro-(E)-7-[4-(4-fluorophenyl)-2,6-diisopropyl-5-methoxy-methyl-pyrid-3-yl] -3,5-dihydroxy-hept-6-enoate is prepared by initially cyclizing a corresponding racemic ester to give the racemic lactones and then separating the latter by chromatography on a chiral stationary phase. Cleavage of the enantiomerically pure lactones with the aid of a base yields the enantiomerically pure end products.

8 Claims, No Drawings

PROCESS FOR PREPARING SODIUM 3R,5S-(+)-ERYTHRO-(E)-7-[4-(4-FLUOROPHENYL)-2,6-DIISOPROPYL-5-METHOXYMETHYL-PYRID-3-YL]-3,5-DIHYDROXY-HEPT-6-ENOATE

The present invention relates to a process for preparing enantiomerically pure sodium 3R,5S-(+)-erythro-(E)-7-[4-(4-fluorophenyl)-2,6-diisopropyl-5-methoxymethyl-pyrid-3-yl]-3,5-dihydroxy-hept-6-enoate.

In European Application EP 491 226, the compound of the formula (I)

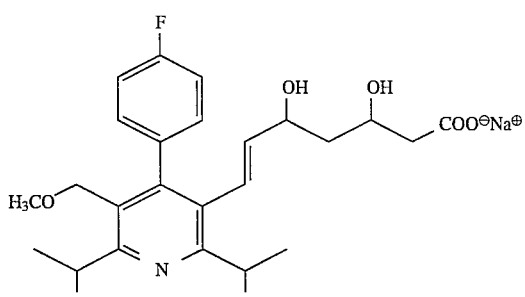

is described, which compound, owing to its property of inhibiting cholesterol biosynthesis, can be employed in medicaments for treating lipoproteinaemia. In this European patent application, this substance is disclosed in the form of its racemate and of the two enantiomers. The racemate is prepared by hydrolysing the corresponding racemic ester, which ester is already described in European Patent Application EP 325 130. The two enantiomers are prepared by reacting the racemic ester with optically active R-(+)-phenylethylamine to give the diastereomeric mixture of the corresponding amides, which amides are in turn separated into the individual diastereomers by customary chromatographic processes. Elimination of the amide group from the separated diastereomers results in the desired enantiomerically pure product. This procedure may be depicted briefly in the following scheme.

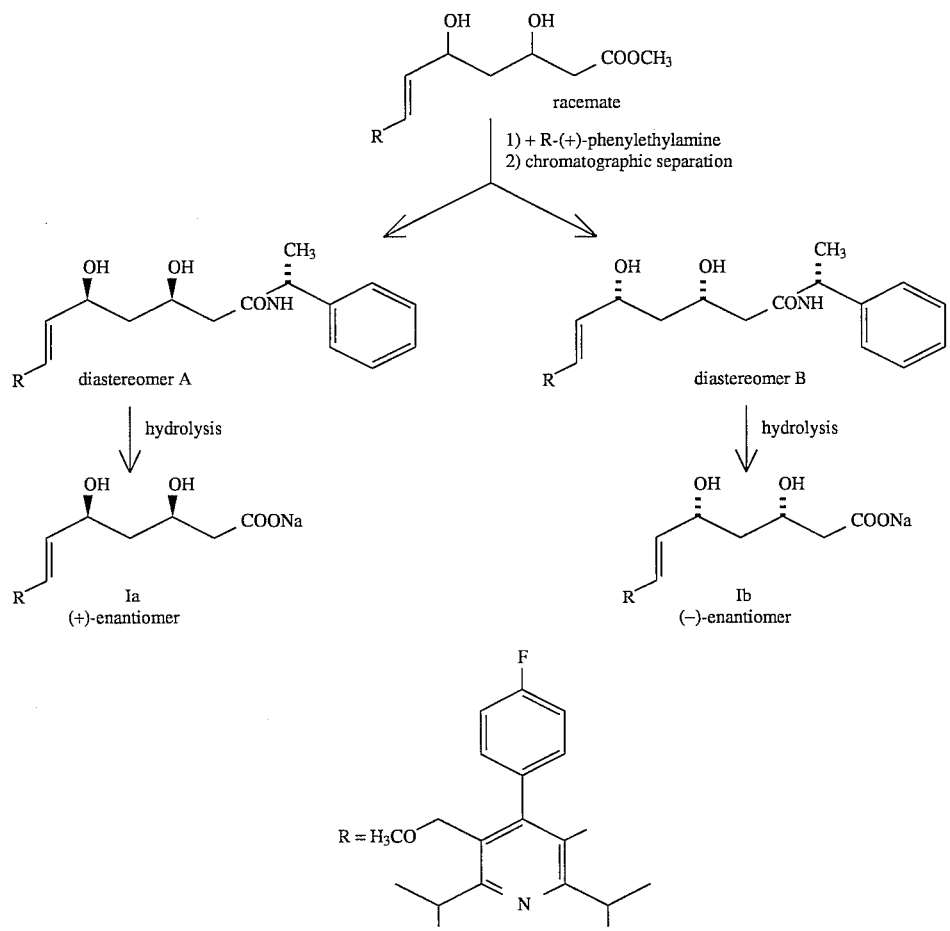

A significant disadvantage of this process is that the racemate cannot be separated directly by chromatography but, instead, an initial conversion into the diastereomeric amides must take place, which amides, following chromatographic separation, can be converted into the pure enantiomers by a further chemical treatment (hydrolysis). This signifies, on the one hand, a technically elaborate procedure and, on the other, a loss in yield, if only due to the fact that two chemical reactions and a chromatographic separation will result in product losses.

It has now been found that sodium 3R,5S-(+)-erythro-(E)-7-[4-(4-fluorophenyl)-2,6 -diisopropyl-5-methoxymethyl-pyrid-3-yl]-3,5-dihydroxy-hept-6-enoate of the formula (Ia)

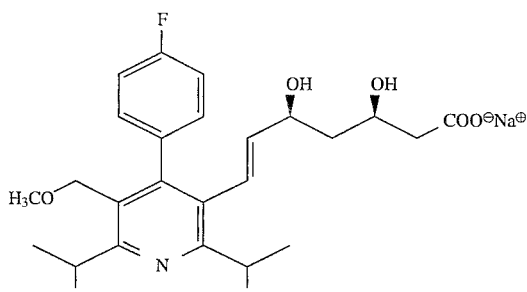
(Ia)

can be prepared in enantiomerically pure form by initially converting racemic esters of the formula (II)

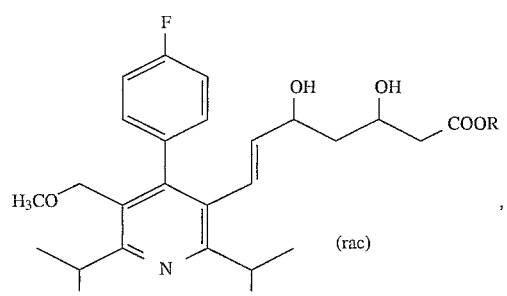
(II)
(rac)

in which
R represents $C_1$–$C_4$-alkyl,
into the racemic lactones of the formula (III),

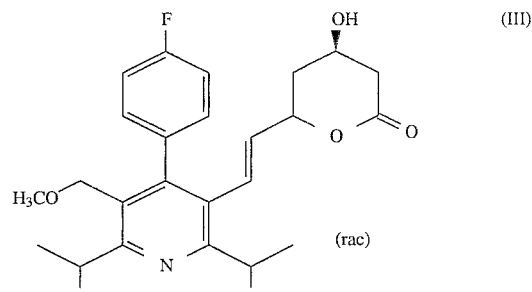
(III)
(rac)

separating this racemate into the individual enantiomeric lactones by chromatography on a chiral phase, and converting each of the enantiomeric lactones by hydrolysis into the desired enantiomerically pure end product.

The process according to the invention can be illustrated by the following scheme:

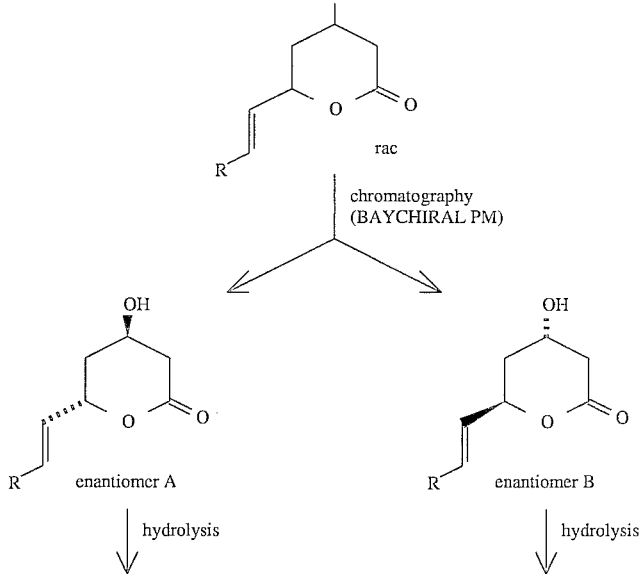

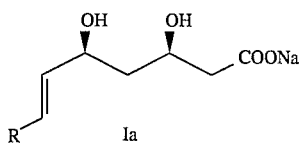 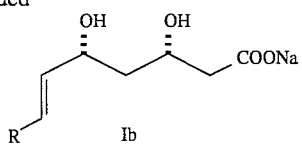

The racemic carboxylic acid esters (III) are in general converted into the racemic lactones (IV) by treating the ester with bases and then cyclizing in suitable solvents, with the elimination of water. In this reaction, the carboxylic acids, or their salts, arise as intermediates.

The customary inorganic bases, such as sodium hydroxide, potassium hydroxide, sodium carbonate or potassium carbonate, are suitable bases for this purpose. Sodium hydroxide is preferably employed.

Ethers, such as, for example, diethyl ether, dioxane or tetrahydrofuran, are suitable solvents for the treatment with a base. The employment of tetrahydrofuran is particularly preferred.

The subsequent cyclization by heating is generally effected in solvents which are not altered under the reaction conditions. These solvents include hydrocarbons, such as benzene, toluene, xylene, petroleum fractions, or tetralin or diglyme or triglyme. The employment of benzene, toluene or xylene is particularly preferred. It is likewise possible to employ mixtures of the said solvents. The use of toluene is particularly preferred. The water which is eliminated in this reaction can be removed by azeotropic distillation or by means of a molecular sieve. Azeotropic distillation is preferred.

The treatment of the esters with bases is generally effected in a temperature range from 0° C. to 50° C., preferably of 10° C. to 30° C., particularly preferably at room temperature.

The cyclization is in general effected in a temperature range from 0° C. to +200° C., preferably of +25° C. to +150° C. It is preferably carried out at the boiling temperature of the azeotropic mixture with water of the solvent used in each case.

The chromatographic separation of the racemic lactones into the individual enantiomerically pure lactones is generally effected on customary chiral materials. These preferably include optically active polymers of optically active (meth)acrylic acid derivatives. Those which are particularly preferred in this instance are polymers of optically active N-(meth)acryloyl-amino acid derivatives, such as are described in EP 379 917. Those which may be mentioned here as being very particularly preferred are polymers of the following optically active N-acryloyl-amino acid esters: N-acryloyl-L-amino acid methyl esters and N-acryloyl-D-amino acid methyl esters, with, for example, leucine, alanine, phenylalanine, valine, or other amino acids, being suitable for use as the amino acid.

Customary organic solvents and solvent mixtures, which cause the polymer employed as the adsorbent to swell and which dissolve the racemate to be designated, are used as the mobile solvent for separating the racemate. Examples which may be mentioned are: hydrocarbons, such as benzene, toluene or xylene, ethers, such as diethyl ether, dioxane or tetrahydrofuran, halohydrocarbons, such as dichloromethane or trichloromethane, acetone, acetonitrile or ethylacetate, or mixtures of the said solvents. Mixtures consisting of toluene and tetrahydrofuran and of toluene and dioxane have proved to be particularly suitable.

The hydrolysis of the respective enantiomerically pure lactone into the desired enantiomerically pure end product is effected in a customary manner using a base in organic solvents.

For this, the customary organic solvents which are not altered under the reaction conditions are suitable for use as solvents. Those which may be mentioned here as being preferred are ethers, such as diethyl ether, dioxane or tetrahydrofuran. The employment of tetrahydrofuran is particularly preferred.

The customary inorganic bases, such as alkali metal hydroxides or alkali metal carbonates, are suitable for use as bases. Sodium hydroxide or potassium hydroxide are preferred.

The hydrolysis is generally effected in a temperature range from 0° C. to +60° C., preferably from +10° C. to +50° C., particularly preferably at room temperature.

The process according to the invention has the advantage that the enantiomerically pure products can be prepared completely without difficulty, and, in particular, without using further reagents, such as, for example, chiral amines, from the racemic esters, the total yield of the inventive process exceeding by far that of the process, known from the state of the art, via diastereomeric amides. In addition to this, the mixture which is to be separated by chromatography does not become contaminated with additional chemicals. A further great advantage is the fact that the corresponding racemic esters can be employed in the form of the crude product for the lactonization.

EXPERIMENTAL PART

Compound 1

Methyl(±)-erythro-(E)-7-[4-(4-fluorophenyl)-2,6-diisopropyl
-5-methoxymethylpyrid -3 -yl]
-3,5-dihydroxy-hept-6-enoate

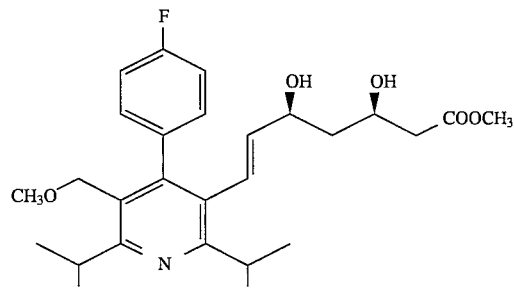

The preparation is effected in analogy with the process described in EP 325 130. However, the crude product can be employed for the subsequent lactonization.

Lactonization

Compound 2

(±)-Trans-(E)-6-[2-(2,6-diisopropyl-4-(4-fluorophenyl)-3-methoxymethylpyrid-5-yl)-ethenyl]-3,4,5,6-tetrahydro-4-hydroxy-2H-pyran-2-one

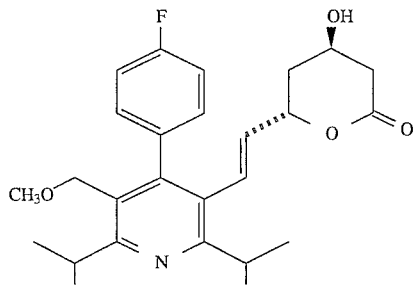

243.3 g (0.52 mol) of crude product of the compound 1 are dissolved in 400 ml of analytical grade tetrahydrofuran and, after adding 520 ml of 1N sodium hydroxide solution, the mixture is stirred at room temperature for 2 h. The tetrahydrofuran is stripped off in vacuo on a rotary evaporator, the aqueous residue is diluted with 200 ml of water, and the mixture is then adjusted to pH 4 with 5N hydrochloric acid. Subsequently, it is extracted three times with 200 ml of methylene chloride and the combined organic phases are dried with sodium sulphate. After concentrating on a rotary evaporator, the residue is taken up in 500 ml of toluene and heated under reflux for 18 h on a water separator. After cooling and concentrating on a rotary evaporator, the solid residue is triturated with cyclohexane and purified through silica gel (1.5 kg, eluent ethyl acetate/petroleum ether 4/6→5/5).

Yield: 144 g of 2 (62.7% of theory).

$^1$H-NMR (CDCl$_3$): δ (ppm)=1.24 (d, 6H); 1.32 (dd, 6H); 1.50 (m, 1H); 1.68 (m, 1H); 2.53 (m, 1H); 2.64 (m, 1H); 3.19 (s, 3H); 3.28 (sept., 1H); 3.37 (sept., 1H); 4.06 (s, 2H); 4.16 (m, 1H); 5.07 (m, 1H); 5.28 (dd, 1H); 6.39 (d, 1H); 7.0–7.2 (m, 4H).

Racemate Separation

Compounds 3 and 4

(+)-trans-(E)-6-[2-(2,6-diisopropyl-4-(4-fluorophenyl)-3-methoxymethyl-pyrid-5-yl)-ethenyl]-3,4,5,6-tetrahydro-4-hydroxy-2H-pyran-2-one (3)

(−)-trans-(E)-6-[2-(2,6-diisopropyl-4-(4-fluorophenyl)-3-methoxymethyl-pyrid-5-yl)-ethenyl]-3,4,5,6-tetrahydro-4-hydroxy-2H-pyran-2-one

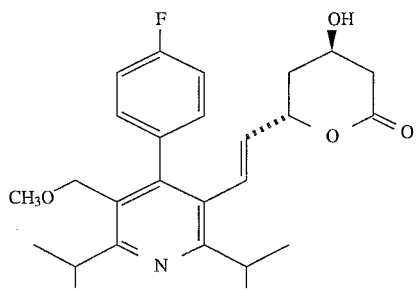

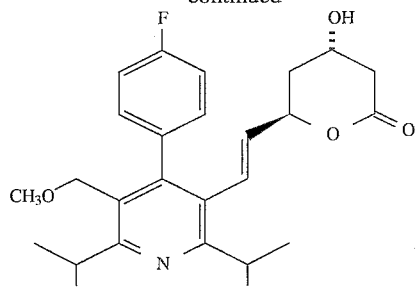

For each run, 6.5 g of the compound of Example 2 are loaded onto a glass column (⌀10 cm, length 40 cm) packed with about 600 g of Baychiral PM (polymer of N-acryloyl-L-phenylalanine α-methyl ester), which is subsequently eluted with toluene/tetrahydrofuran 5/1 at a flow rate of 3.5 ml/min. A separation takes about 7.5 h, so that 20 g can be separated in one day. In this procedure, the enantiomers are separated virtually down to the base line. The combined product fractions are concentrated and dissolved in a minimal quantity of methyl tert-butyl ether. 3 is precipitated out by adding n-heptane and subsequently filtered off with suction and dried.

Yield: 3.05 g (47.5%).

Specific rotation (CDCl$_3$): [d]$^{20}$=35.7° C. (c=1).

The (−)-lactone 4 can be obtained in an analogous manner by combining the corresponding product fractions.

Specific rotation (EtOH): [d]$^{20}$=29.9° (c=1).

Hydrolysis

Compound 5

Sodium 3R,5S-(+)-erythro-(E)-7-[4-[(4-fluorophenyl)-2,6-diisopropyl-5-methoxymethyl-pyrid-3-yl]-3,5-dihydroxy-hept-6-enoate

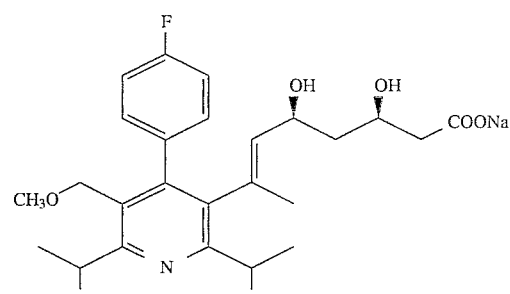

121.5 g (0.276 mol) of the compound 3 are dissolved in 100 ml of absol. tetrahydrofuran and, after adding 276 ml of 1 N sodium hydroxide solution and 724 ml of distilled water, the mixture is stirred at room temperature for 1.5 h. The tetrahydrofuran is then stripped off in vacuo and the remaining aqueous solution is frozen and freeze-dried. The lyophilisate is then dried over phosphorus pentoxide.

Yield: 132.6 g (99.8%).

Specific rotation (EtOH): [d]$^{20}$=22.8° (c=1).

We claim:

1. A process for preparing sodium 3R,5S-(+)-erythro-(E)-7-[4-(4-fluorophenyl)- 2,6-diisopropyl-5-methoxymethyl-pyrid-3-yl]-3,5-dihydroxy-hept-6-enoate of the formula

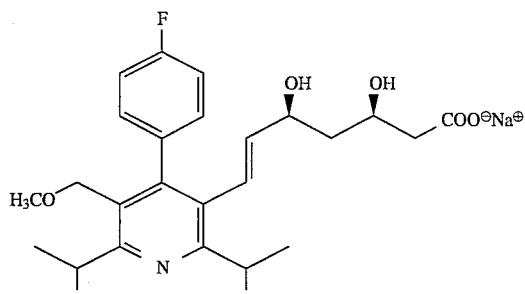

(Ia)

which is an enantiomerically pure form which comprises initially converting racemic esters of the formula (II)

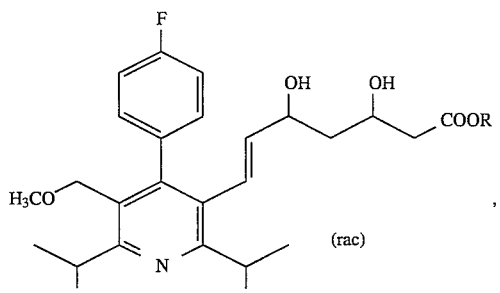

(II)

in which

R represents $C_1$–$C_4$-alkyl, into the racemic mixture of lactones of the formulae

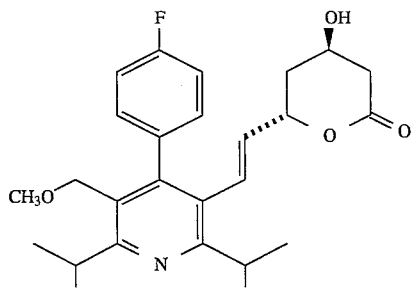

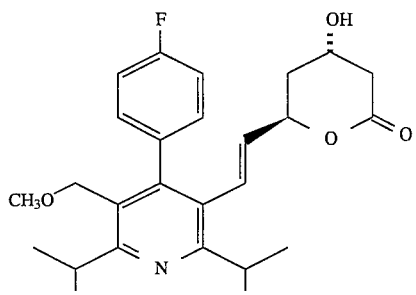

separating this racemate into the individual enantiomeric lactones by chromatography on a chiral phase and converting the enantiomeric lactones, in each case by hydrolysis, into the desired enantiomerically pure end product.

2. Process according to claim 1, wherein sodium hydroxide is used as the base in the first step.

3. Process according to claim 1, wherein the reaction with the base is carried out in tetrahydrofuran.

4. Process according to claim 1, wherein the cyclization is carried out in toluene.

5. Process according to claim 1, wherein the cyclization is carried out in a temperature range from 0° C. to +200° C.

6. Process according to claim 1, wherein a bead polymer consisting of N-acryloyl-amino acid esters is used as the chiral phase for the chromatographic separation.

7. Process according to claim 1, wherein a bead polymer consisting of N-acryloyl-L-phenyl alanine α-methyl ester is used as the chiral phase.

8. Process according to claim 1, wherein mixtures of toluene and dioxane, or of toluene and tetrahydrofuran, are employed as the mobile solvent for separating the racemate.

* * * * *